United States Patent [19]

Berchem

[11] Patent Number: 4,946,379

[45] Date of Patent: Aug. 7, 1990

[54] JOINT PROSTHESES ESPECIALLY HIP JOINT PROSTHESES

[75] Inventor: Rütger Berchem, Essen, Fed. Rep. of Germany

[73] Assignee: Metalpraecis Berchem & Schaberg Gesellschaft Für Metallformgebung Mit Beschrankter Haftung, Gelsenkirchen-Ückendorf, Fed. Rep. of Germany

[21] Appl. No.: 331,401

[22] Filed: Mar. 30, 1989

[30] Foreign Application Priority Data

Apr. 1, 1988 [DE] Fed. Rep. of Germany ....... 3811207

[51] Int. Cl.$^5$ ............................................... A61F 2/30
[52] U.S. Cl. .......................................... 623/18; 623/23
[58] Field of Search ...................... 623/16, 18, 20, 22, 623/23

[56] References Cited

U.S. PATENT DOCUMENTS

| 4,530,115 | 7/1985 | Muller et al. | 623/23 |
| 4,532,661 | 8/1985 | Halpern | 623/23 |
| 4,698,063 | 10/1987 | Link et al. | 623/23 |

FOREIGN PATENT DOCUMENTS

| 2611985 | 9/1977 | Fed. Rep. of Germany | 623/23 |
| 2839092 | 3/1980 | Fed. Rep. of Germany | 623/23 |
| 3432930 | 3/1986 | Fed. Rep. of Germany | 623/20 |
| 1099519 | 9/1955 | France | 623/23 |

Primary Examiner—David J. Isabella
Attorney, Agent, or Firm—Herbert Dubno

[57] ABSTRACT

A joint prosthesis insertable, for example, in the marrow cavity of the femur, has a shaft formed with three longitudinally extending angularly equispaced contact surfaces by reason of a triangular of Y section. A statically determinate engagement of the prosthesis shaft in the bone is thus obtained.

4 Claims, 2 Drawing Sheets

JOINT PROSTHESES ESPECIALLY HIP JOINT PROSTHESES

CROSS-REFERENCE TO RELATED APPLICATION

This application is related to my commonly assigned copending application Ser. No. 07/276,187, filed November 23, 1988.

1. Field of the Invention

My present invention relates to a joint prosthesis and, more particularly, to a hip joint prosthesis of the type which has a shaft which can be driven into the marrow passage of, for example, the femur or, more generally, the bone to be provided with the prosthesis.

2. Background of the Invention

In the art of joint replacement, it is known to provide a hip joint prosthesis which comprises a shaft which can be inserted into the marrow passage of the femur, for example, a closure plate which is designed to close the transected end of the bone into which the shaft is inserted, and a ball joint fitting, e.g. a ball or pin adapted to carry the ball, which forms one half of the joint while a socket engageable with the ball forms the other half of the joint.

The femoral joint element can be cemented in place or held in place without cement and the ball part can be rigidly connected with the closure plate or the shaft or can be replaceable thereon.

The earlier joint prostheses over which the present invention represents an improvement, comprise a shaft having generally round cross section and tapering downwardly, i.e. toward the end of the shaft opposite that provided with the ball part.

However, the marrow cavity in the bone is not perfectly round.

As a result, indeterminate relationships are established between the parts of the wall of the marrow cavity and the shaft which contact one another and a statically indeterminate structure can result, because the contact between the shaft and the wall of the marrow cavity may be exclusively point contacts.

This gives rise to a variety of drawbacks whether the joint prosthesis is cemented in place or held in place by a cement-free connection.

Upon cementing in place, there may remain an envelope curve about 1 mm in thickness around the shaft. To this extent, therefore, the cement layer can compensate for irregularities in the shape of the shaft and in the wall of the marrow cavity and, of course, irregularities in the configuration of the latter after preparation. Nevertheless, because of the statically indeterminate engagement of the bone with the shaft, loosening can occur with variable loading as may eventuate in the use of the joint.

With a cement-free system, the failure of the attachment may even occur earlier because of the indeterminate engagement.

Indeed, attempts have been made to shape the marrow cavity by variety of preparative steps to conform to the shaft and vice-versa, thereby providing bearing surfaces between the shaft and the bone. This has not proved to be fully successful either.

In practice, it is found that the point contact leads to calcification and then to breakage of the bone.

Thus with earlier systems, whether utilizing a cemented technique or a noncemented approach, even with some measure of attempting to match the shape of the marrow cavity and the shape of the shaft, the attachment of the shaft to the bone is inadequate to tolerate the loads to which the joint would be subject and can result in breakage of the bone and hence failure of the joint.

OBJECTS OF THE INVENTION

It is, therefore, the principal object of the present invention to provide an improved joint prosthesis which can obviate the drawbacks outlined above.

Still another object of the invention is to provide a joint prosthesis with statically determinate engagement and anchorage of the shaft in the marrow cavity and which, because of the statically determinate engagement of the shaft of the prosthesis can obviate the problems hitherto encountered with such prostheses.

SUMMARY OF THE INVENTION

These objects and others which will become apparent hereinafter are attained, in accordance with the invention, by a joint prosthesis adapted to be inserted into a marrow cavity of a bone which comprises:

an elongated shaft receivable in a marrow cavity of a bone at one end thereof and adapted to form one side of a joint, the shaft having an end at the end of the bone, the shaft being formed at least at the end thereof with a cross section having three contact surfaces engageable with an inner surface of the marrow cavity, the contact surfaces extending longitudinally along the shaft substantially parallel to a longitudinal axis thereof;

a closure plate on the end of the shaft adapted to close the end of the bone; and ball-joint means on the closure plate for engagement in a socket formation adapted to form the other side of the joint.

Thus the shaft of the present invention is so shaped that three longitudinally extending prominences, ridges or ledges form engagement surfaces of limited width, i.e. a peripheral width which is substantially less than the perimeter of the shaft, for contact with the inner surface or wall of the marrow passage, these contact surfaces extending substantially to the longitudinal axis of the shaft.

These longitudinally extending convex contact surfaces can be developed in different ways and especially provided at the top of the shaft, although they most advantageously extend the full length thereof.

In accordance with one embodiment of the invention, the shaft has a generally triangular cross section and the vertices of the triangular cross section are rounded or shaped to form the contact for engagement surfaces.

In another embodiment of the invention, the shaft has a Y-shaped cross section with arms or webs of the Y formed with the rounded convex contact surfaces.

The arrangement is such that the portions of the shaft lying adjacent the contact surfaces do not come into contact with the wall of the cavity of the bone.

To allow a firm engagement especially in the vertical direction, the contact surfaces especially in the region directly below the closure plate can be formed with sawteeth formations or serrations adapted to bite into the aforementioned wall of the marrow cavity.

Furthermore, to secure the prosthesis against twisting in the marrow cavity, the shaft immediately below the closure plate and/or the closure plate at its junction with the shaft and at its underside, can be provided with antirotation elements, e.g. projections, which engage the bone.

Since only the longitudinally extending narrow convex contact surfaces at three equispaced zones engage the bone, a statically indeterminate structure is provided according to the invention. The contact surfaces simultaneously function as rails which facilitate insertion of the shaft.

The contact between the contact surfaces and the wall of the marrow cavity is essentially a line contact with a contact pressure per unit area spread over the width of the contact surface.

The result is a wedging of the shaft in the marrow cavity and a firm and distributed contact between the wall of the latter and the prosthesis which avoids all of the drawbacks enumerated above.

The invention is applicable particularly to so-called individual hip prostheses which are prostheses designed for the particular body weight and load expectations of the patient.

The prosthesis can be cemented in place or held in place by a cement-free connection. When cementing in place is desirable, the cement can fill the spaces between the flanks of the triangular cross section and the wall of the marrow cavity or the spaces between the arms of the Y and the wall of the marrow cavity.

BRIEF DESCRIPTION OF THE DRAWING

The above objects, features and advantages of my invention will become more readily apparent from the following description, reference being made to the accompanying drawing in which.

SPECIFIC DESCRIPTION

Figure 1:
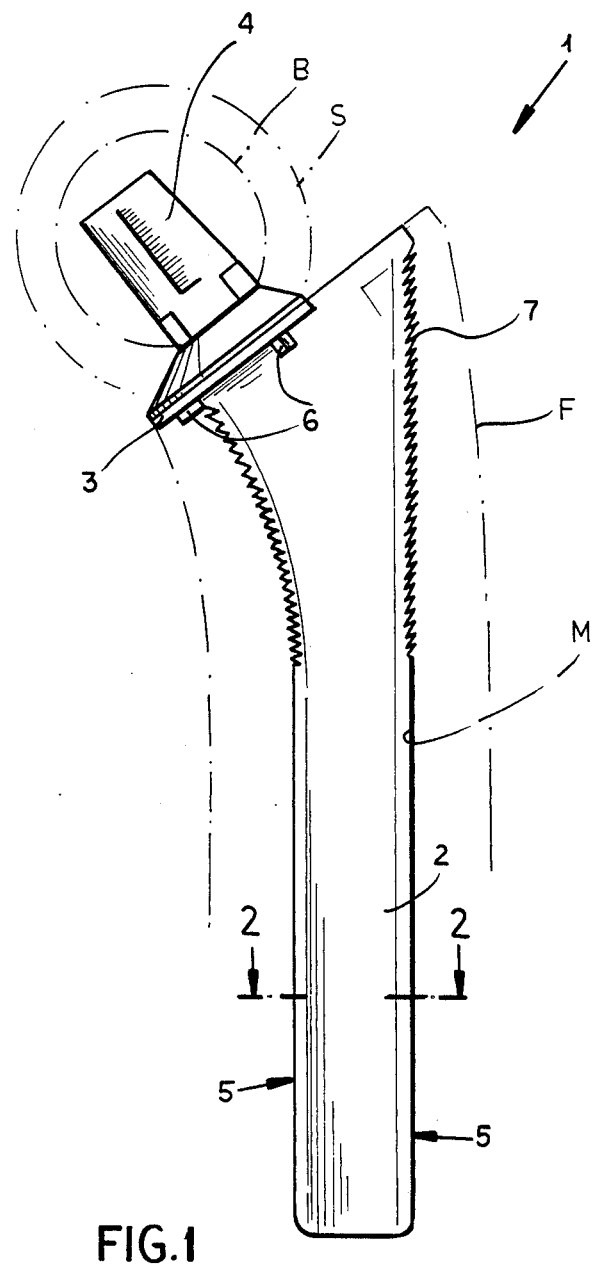
FIG. 1 is a side-elevational view.

The hip joint prosthesis shown in FIG. 1 at 1 is intended to be anchored in the marrow cavity of a femur F whose upper end may be transected for this purpose. The marrow cavity is only indicated at M in FIG. 1. The prosthesis can be held in place by cementing or in a cement-free manner.

The prosthesis 1 comprises a shaft 2 which can be inserted into the marrow cavity M and is equipped at its upper end with a closure plate 3 and a ball joint fitting 4 upon which a removable ball B may be fixed (see the aforementioned copending application).

The other part of the joint has been represented by a socket S engageable with a ball.

Figure 2:
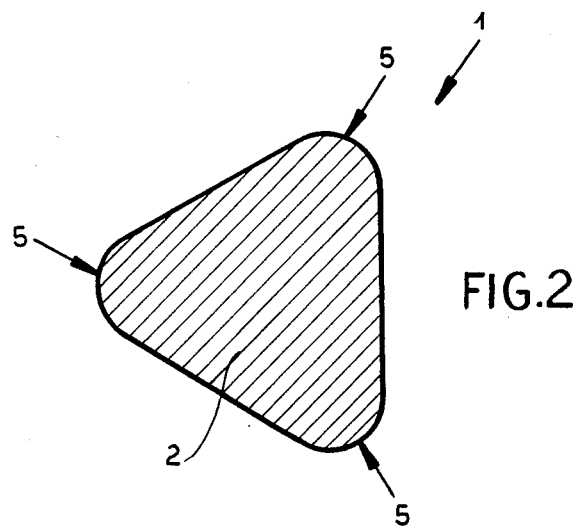
FIG. 2 is a cross-sectional view taken generally along the line II—II of FIG. 1.
Figure 3:
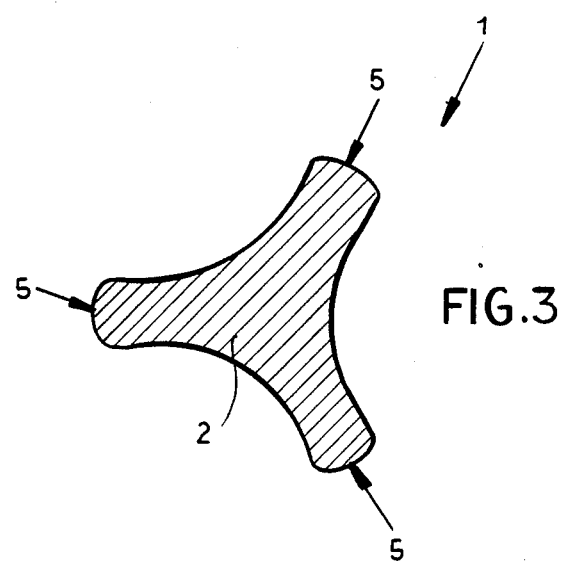
FIG. 3 is a cross-sectional view of another embodiment of the invention in a simultaneous.

As can be seen from a comparison of FIGS. 1-3, the shaft 2 has a cross section clearly defining three contact surfaces 5 for engagement with the inner surface of the wall surrounding the marrow cavity.

The arrangement is so constituted that the contact surfaces 5 extend substantially parallel to the longitudinal axis of the shaft 2.

In the embodiment of FIGS. 1 and 2, the shaft 2 is shown to have a triangular cross section with the vertices of the triangle rounded-off to form the contact surfaces 5.

In the embodiment of FIG. 3, the shaft 2 is shown to have a Y-shaped cross section. The outer edges or surfaces of the arms of the Y or the webs thereof are formed into the contact surfaces.

From FIG. 1, it will be apparent that the contact surfaces 5 in the region below the plate 3 are profiled with saw tooth formations 7.

Furthermore, on the shaft directly below the plate 3 or on the underside of the plate 3 or both, projections 6 are provided to engage the bone and prevent rotation of the prosthesis in the bone.

I claim:

1. An implantable joint prosthesis for insertion into a prepared intramedullary cavity comprising:
    a ball joint means for engagment in a corresponding socket;
    an elongated shaft having a longitudinal axis and terminating at opposite proximal and distal ends;
    a collar disposed at the proximal end of said shaft intermediate said ball joint means and said shaft, said collar having a bottom surface configured to seat on a resected surface on the bone; and
    at least a proximal portion of said shaft having a generally triangular uniform cross-section, said cross-section defining three convex contact surfaces formed on respective vertices thereof wherein each of the contact surfaces having sawtooth profiling thereon for engaging the inner surface of the intramedullary cavity.

2. The joint prosthesis defined in claim 1 wherein said collar is formed with antirotation means extending distally and substantially perpendicular from said bottom surface to engage said bone.

3. An implantable joint prosthesis for insertion into a prepared intramedullary cavity comprising:
    a ball joint means for engagment in a corresponding socket;
    an elongated shaft having a longitudinal axis and terminating at opposite proximal and distal ends;
    a collar disposed at the proximal end of said shaft intermediate said ball joint means and said shaft, said collar having a bottom surface configured to seat on a resected surface of the bone; and
    at least a proximal portion of said shaft having three equal armed Y-shaped uniform cross-section, said cross-section defining three convex contact surfaces formed on respective edges of said arms thereof wherein each of the contact surfaces having sawtooth profiling thereon for engaging the inner surface of the intramedullary cavity.

4. The joint prosthesis defined in claim 3 wherein said collar is formed with antirotation means extending distally and substantially perpendicular from said bottom surface to engage said bone.

* * * * *